United States Patent [19]
Brown

[11] 3,939,155
[45] Feb. 17, 1976

[54] 4',5'-DIHYDROSPIRO[ANDROST/ESTR-4-ENE-17,2'(3'H)-FURAN]3,4'-DIONE AND CONGENERS, AND INTERMEDIATES THERETO

[75] Inventor: Edward A. Brown, Glenview, Ill.

[73] Assignee: G. D. Searle & Co., Chicago, Ill.

[22] Filed: June 28, 1974

[21] Appl. No.: 483,986

[52] U.S. Cl. .................. 260/239.55 R; 424/241
[51] Int. Cl.² ................................... C07J 21/00
[58] Field of Search ................... 260/239.55 R

[56] References Cited
UNITED STATES PATENTS

| | | | |
|---|---|---|---|
| 3,074,936 | 1/1963 | Zderic et al. ............... | 260/239.57 |
| 3,137,690 | 6/1964 | Johns ........................... | 260/239.55 |
| 3,238,197 | 3/1966 | Arth ............................. | 260/239.55 |
| 3,254,074 | 5/1966 | Arth ............................. | 260/239.55 |
| 3,757,009 | 9/1973 | Anner ......................... | 260/239.55 R |

*Primary Examiner*—Ethel G. Love
*Attorney, Agent, or Firm*—John M. Brown

[57] ABSTRACT

4',5'-Dihydrospiro[androst/estr-4-ene-17,2'(3'H)-furan]-3,4'-dione and congeners; the antiviral, antiandrogenic, diuretic, and/or antiestrogenic activity inherent therein; and means of preparing them via novel intermediates are disclosed.

10 Claims, No Drawings

4',5'-DIHYDROSPIRO[ANDROST/ESTR-4-ENE-17,2'(3'H)-FURAN]3,4'-DIONE AND CONGENERS, AND INTERMEDIATES THERETO

This invention relates to 4',5'-dihydrospiro[androst-/estr-4-ene-17,2'(3'H)-furan]-3,4'-dione and congeners, intermediates thereto, and processes for their preparation. More particularly, this invention provides steroids of the formula

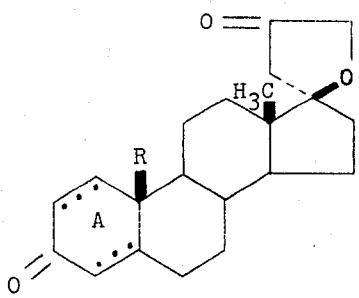

wherein R represents hydrogen or methyl and the dotted lines in ring A indicate $\Delta^4$ unsaturation when R represents hydrogen and $\Delta^1$, $\Delta^4$, or $\Delta^{1,4}$ unsaturation when R represents methyl.

The enformulated compounds are useful by reason of their valuable biological properties. Thus, the compound contemplated when R in the foregoing formula represents hydrogen is an especially potent antiestrogen. It is also antiandrogenic and diuretic. On the other hand, the compounds contemplated when R in the formula represents methyl are antiviral — as, for example, vis-a-vis Influenza A (Strain 575). Other steroids disclosed herein are valuable as intermediates to the enformulated compounds.

Antiestrogenic utility is demonstrated by the procedure described in U.S. Pat. No. 3,475,420. The subcutaneous antiestrogenic potency of the product of Example 3F hereinafter was found to be 170 times that of progesterone in the aforesaid test.

Diuretic utility can be demonstrated by a standardized test for the capacity of a compound to reverse the renal electrolyte effects of desoxycorticosterone acetate (DCA) in rats. Such a test, substantially as described by C. M. Kagawa in chapter 34 of volume III of "Evaluation of Drug Activities: Pharmacometrics", by D. R. Laurence and A. L. Bacharach, can be carried out as follows. A group (Group I) of eight male Charles River rats, each weighing between 150 and 200 gm, is adrenalectomized and maintained thereafter on sugar cubes and tap water ad libitum overnight. Each animal is thereupon subjected to these successive treatments: (a) 0.012 mg of DCA dissolved in 0.1 ml of corn oil is injected subcutaneously; (b) 2.4 mg of test compound dissolved or suspended in 0.5 ml. of corn oil or other physiologically inert solvent (e.g., aqueous 0.9% sodium chloride), is administered subcutaneously or intragastrically; (c) 2.5 ml of aqueous 0.9% sodium chloride is injected subcutaneously. Urinary sodium and potassium are measured by customary techniques on samples of urine collected during the 4 hr. immediately following treatment. Controls are provided by second and third groups of 8 each 150–200 gm rats concurrently and identically treated excepting that in Group II, 0.33 mg of spironolactone is substituted for the test compound and the solution thereof is injected subcutaneously, while in Group III neither test compound nor spironolactone is administered. DCA produces sodium (Na) retention, loss of potassium (K), and a corresponding reduction in the mean log Na × 10/K. Spironolactone serves as an index of the validity of the test, the dose of 0.33 mg having been shown [Hofmann et al., Arch. intern. pharmacodynamie, 165, 476 (1967)] to induce a 50% reversal of the effects of DCA. Kagawa [Endocrinology, 74, 724 (1964)] reported a standard error of ± 0.084 per 4-rat response, determined from a large number of tests and based on 60° of freedom, for the mean log Na × 10/K measurement. From this it can be calculated that the least significant difference (P < 0.05) in mean log Na × 10/K between 2 groups of 8 rats each is ± 0.168. It follows that when mean log Na × 10/K for Group I is equal to or greater than that for Group II, and the latter in turn exceeds the value for Group III by at least 0.168 log units, the reversals of the renal electrolyte effects of DCA represented thereby are significant. A compound active at the 2.4 mg dose level is retested at lower doses until the median effective dose (MED), a dose in mg sufficient to produce a 50% inhibition of the renal electrolyte effects of the DCA administered, can be calculated. The subcutaneous MED of the product of Example 3F in the foregoing test for diuretic activity was found to be 0.87 mg.

Antiandrogenic utility can be demonstrated by a standardized test for the capacity of a compound to inhibit the response of the seminal vesicle glands to intramuscular testosterone propionate in castrated immature rats. Male Sprague-Dawley rats, castrated at 22–24 days of age, are used. To each of a group of 5 or more such animals beginning 19–21 days after castration, a solution of 0.5 mg of testosterone propionate in 0.7 ml of corn oil and the compound to be tested are concurrently administered in equally divided doses on each of 7 successive days. Administration of the compound is either intramuscular or intragastric. If intramuscular, it is dissolved or suspended in the testosterone propionate solution; if intragastric, it is dissolved or suspended in corn oil or other physiologically inert vehicle. Commonly, the initial total dose of compound is 5 mg in 0.7 ml of corn oil administered intramuscularly or 15 mg in 1.4 ml of corn oil administered intragastrically. A second group of 5 or more animals, to which only the corn oil solution of testosterone propionate is administered, serves as controls. On the day after treatment is concluded, the animals are sacrificed; and the seminal vesicle glands are excised and dissected free of extraneous tissue. Fluid is expressed from the vesicles, whereupon the glands are blotted and weighed. A compound is considered antiandrogenic if the mean weight of the vesicles in the group of animals treated therewith is significantly (P ≤ 0.01) lower than the corresponding weight in the control group. The product of Example 3F was found to be antiandrogenic at 10 mg subcutaneously in this test.

Antiviral utility vis-a-vis Influenza A (Strain 575) is demonstrable by the standardized test procedure described in U.S. Pat. No. 3,691,207. The products of Example 1D hereinafter were found to be active subcutaneously at concentrations ranging from 25 to 125 mcgm per ml when so tested.

Those skilled in the art will recognize that observations of activity in standardized tests for particular biological effects are fundamental to the development of valuable new drugs, both veterinary and human.

The compounds of this invention defined by the introductory formula when R therein represents methyl can be prepared as follows: 21-(Hydroxymethyl)-5α,17α-pregn-20-ene-3β,17-diol, upon prolonged contact with p-toluenesulfonyl chloride in pyridine, affords spiro[5α-androstane-17,2'(5'H)-furan]-3β-ol, from which, upon consecutive contact in cold tetrahydrofuran under nitrogen with borane and sodium peroxide (formed in situ), 4',5'-dihydrospiro[5α-androstane-17,2'(3'H)-furan]-3β,4'-diol is obtained. The hydroxyls therein are oxidized to oxos with Jones' reagent (prepared by dissolving 10 parts of chromium trioxide in 20 parts of water and consecutively adding to the resultant solution 15 parts of concentrated sulfuric acid and 20 parts of water) in acetone. The 4',5'-dihydrospiro[5α-androstane-17,2'(3'H)-furan]-3,4'-dione thus obtained, upon heating in dioxane under nitrogen with dichlorodicyanobenzoquinone, affords a mixture of 4',5'-dihydrospiro[5α-androst-1-ene-17,2'(3'H)-furan]-3,4'-dione and 4',5'-dihydrospiro[androsta-1,4-diene-17,2'(3'H)-furan]-3,4'-dione, separable by chromatography. The $\Delta^{1,4}$ product, consecutively contacted in tetrahydrofuran with liquid ammonia and lithium, affords 4',5'-dihydrospiro[androst-4-ene-17,2'(3'H)-furan]-3,4'-dione.

The compound of this invention defined by the introductory formula when R therein represents hydrogen can be prepared as follows: 21-(Hydroxymethyl)-3-methoxy-17α-pregna-1,3,5(10),20-tetraen-17-ol, upon prolonged contact with p-toluenesulfonyl chloride in pyridine, affords 3-methoxyspiro[estra-1,3,5(10)-triene-17,2'(5'H)-furan]. Consecutively contacting the latter intermediate in cold tetrahydrofuran under nitrogen with borane and sodium peroxide (formed in situ) affords 4',5'-dihydro-3-methoxyspiro[estra-1,3,5(10)-triene-17,2'(3'H)-furan]-4'-ol, from which, upon consecutively contacting in tetrahydrofuran and 1,1-dimethylethanol with liquid ammonia and lithium, 4',5'-dihydro-3-methoxyspiro[estra-2,5(10)-diene-17,2'(-3'H)-furan[-4'-ol is obtained. Conversion of this enol ether to the corresponding 5(10)-en-3-one occurs upon contact with 90% acetic acid, and from the 4',5'-dihydro-4'-hydroxyspiro[estr-5(10)-ene-17,2'(3'H)-furan]-3-one thus obtained, 4',5'-dihydro-4'-hydroxyspiro[estr- 4-ene-17,2'(3'H)-furan]-3-one eventuates on contact with hydrochloric acid in methanol. Finally, the hydroxyl therein is oxidized with Jones' reagent in acetone, affording 4',5'-dihydrospiro[estr-4-ene-17,2'(3'H)-furan]-3,4'-dione.

The following examples describe in detail compounds illustrative of the present invention and methods which have been devised for theier preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. A solution of 36 parts of 21-(Hydroxymethyl)-5α,17α-pregn-20-ene-3β,17-diol [Helv. Chim. Acta, 27, 24 (1944)] and 36 parts of p-toluenesulfonyl chloride in 350 parts of pyridine is allowed to stand at room temperatures for 24 hours, then poured into 2000 parts of ice-water. The precipitate which forms is isolated by filtration, washed with water, and dried in air, whereupon it is taken up in benzene. The benzene solution is chromatographed on silica gel, using benzene and mixtures thereof with increasing amounts of ethyl acetate as developing solvent. From an eluate comprising 10% ethyl acetate in benzene, on evaporation of solvent and recrystallization of the residue from ethyl acetate, spiro[5α-androstane-17,2'(5'H)-furan]-3β-ol melting at 165°–170° is obtained.

B. To a solution of 196 parts of spiro[5α-androstane-17,2'(5'H)-furan]-3β-ol in 6300 parts of tetrahydrofuran at 5°–10° is added, with stirring, a solution of approximately 10 parts of borane in 630 parts of tetrahydrofuran. Stirring at 5°–10° is continued for 2 hours, whereupon a solution of 50 parts of sodium hydroxide in 420 parts of water, followed by 264 parts of 30% hydrogen peroxide, is added. The resultant mixture is acidified with 20% hydrochloric acid, then poured into 60,000 parts of ice water. The precipitate which forms is isolated by filtration, washed with water, dried in air, and recrystallized from a mixture of methanol and acetone to give 4',5'-dihydrospiro[5α-androstane-17,2'(3'H)-furan]-3β,4'-diol, melting at 202°–213°.

C. To a solution of 18 parts of 4',5'-dihydrospiro[5α-androstane-17,2'(3'H)-furan]-3β,4'-diol in 1600 parts of acetone is cautiously added, with stirring, 64 parts of Jones' reagent. After the addition is complete, stirring is continued for 10 minutes, and thereafter while 15 parts of 2-propanol followed by 10,000 parts of water are introduced. The precipitate which forms is isolated by filtration, washed with water, dried in air, and recrystallized from ethyl acetate to give 4',5'-dihydrospiro[5α-androstane-17,2'(3'H)-furan]-3,4'-dione melting at 141°–144°.

D. A mixture of 1 part of 4',5'-dihydrospiro[5α-androstane-17,2'(3'H)-furan]-3,4'-dione and 1 part of dichlorodicyanobenzoquinone in 16 parts of dioxane is heated at the boiling point under reflux in a nitrogen atmosphere with stirring, then cooled to room temperature and filtered. The filtrate is diluted with 55 parts of ether. The resultant solution is consecutively washed with water, aqueous 2% sodium sulfite, and water, then dried over anhydrous sodium sulfate and finally stripped of solvent by vacuum distillation. The residue is taken up in benzene; and the benzene solution is chromatographed on silica gel, using benzene and mixtures thereof with increasing amounts of ethyl acetate as developing solvents. From an eluate comprising 5% ethyl acetate in benzene, on evaporation of solvent and recrystallization of the residue from ethyl acetate, 4',-5'-dihydrospiro[5α-androst-1-ene-17,2'(3'H)-furan]-3,4'-dione, having the formula

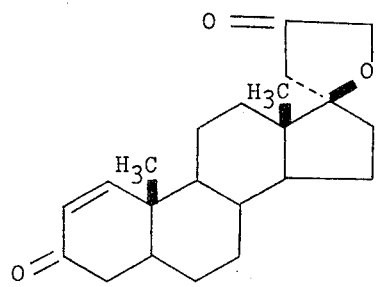

is obtained.

From an eluate comprising 10% ethyl acetate in benzene, on evaporation of solvent and recrystallization of the residue from ethyl acetate, 4',5'-dihydrospiro[androsta-1,4-diene-17,2'(3'H)-furan]-3,4'-dione melting at 147°–153° is obtained.

EXAMPLE 2

To 1700 parts of liquid ammonia under reflux is added, portionwise with stirring, 10 parts of lithium. When solution occurs, a solution of 34 parts of 4',5'-dihydrospiro[androst-1,4-diene-17,2'(3'H)-furan]-3,4'-dione in 2250 parts of tetrahydrofuran is rapidly introduced. Shortly thereafter, 10 parts of ammonium chloride is added. The ammonia is thereupon allowed to evaporate, and the residue is diluted with 10,000 parts of water. Insoluble solids are isolated by filtration, washed with water, dried in air, and recrystallized from ethyl acetate. The product thus isolated is 4',5'-dihydrospiro[androst-4-ene-17,2'(3'H)-furan]-3,4'-dione.

EXAMPLE 3

A. A solution of 2 parts of 3-methoxy-17α-pregna-1,3,5(10),20-tetraen-21-ol [U.S. Pat. No. 3,265,718] and 2 parts of p-toluenesulfonyl chloride in 20 parts of pyridine is allowed to stand at room temperatures for 70 hours, then poured into 150 parts of ice-water. The precipitate which forms is isolated by filtration, washed with water, dried in air, and recrystallized from ethyl acetate to give 3-methoxyspiro[estra-1,3,5(10)-triene-17,2'(5'H)-furan] melting at 159°–161°.

B. To a solution of 116 parts of 3-methoxyspiro[estra-1,3,5(10)-triene-17,2'(5'H)-furan] in 1100 parts of tetrahydrofuran at 5°–10° under nitrogen is added, with stirring, a solution of approximately 5 parts of borane in 325 parts of tetrahydrofuran. Stirring at 5°–10° is continued for 2¼ hours, whereupon a solution of 26 parts of sodium hydroxide in 213 parts of water followed — cautiously — by 131 parts of 30% hydrogen peroxide is mixed in. The resultant mixture is acidified with 20% hydrochloric acid and then poured into 7000 parts of ice water. The precipitate which forms is isolated by filtration, washed with water, dried in air, and taken up in benzene. The benzene solution is chromatographed on silica gel, using benzene and mixtures thereof with increasing amounts of ethyl acetate as developing solvents. From an eluate comprising 10% ethyl acetate in benzene, on evaporation of solvent and recrystallization of the residue from ethyl acetate, 4',5'-dihydro-3-methoxyspiro[estra-1,3,5(10)-triene-17,2'(3'H)-furan]-4'-ol melting at 95°–97° is obtained.

C. To 122 parts of liquid ammonia under reflux is added, with vigorous agitation, a solution of 3 parts of 4',5'-dihydro-3-methoxyspiro[estra-1,3,5(10)-triene 17,2'(3'H)-furan]-4'-ol in a mixture of 81 parts of tetrahydrofuran and 72 parts of 1,1-dimethylethanol, followed — portionwise — by 2 parts of lithium wire cut into small pieces. Approximately 2 hours later, 5 parts of methanol is slowly introduced. After an additional 45 minutes, the blue color originally characteristic of the reaction mixture has disappeared, at which point the ammonia is allowed to evaporate and 500 parts of water is added to the residue. The precipitate which forms is filtered off, washed with water, dried in air, and recrystallized from ethyl acetate to give 4',5'-dihydro-3-methoxyspiro[estra-2,5(10)-diene-17,2'(-3'H)-furan]-4'-ol melting at 152°–155°.

D. A suspension of 1 part of 4',5'-dihydro-3-methoxyspiro[estra-2,5(10)-diene-17,2'(3'H)-furan]-4'-ol in 20 parts of aqueous 90% acetic acid is stirred for 1¾ hours, during which solution occurs. Approximately 100 parts of cold water is thereupon introduced, whereupon the precipitate which forms is filtered off, washed with water, dried in air, and recrystallized from ethyl acetate to give 4',5'-dihydro-4'-hydroxyspiro[estr-5(10)-ene-17,2'(3'H)-furan]-3-one melting at 118°–123°.

E. A mixture of 15 parts of 4',5'-dihydro-4'-hydroxyspiro[estr-5(10)-ene-17,2'(3'H)-furan]-3-one, 79 parts of methanol, 8 parts of concentrated hydrochloric acid, and 5 parts of water is allowed to stand at room temperatures for 2 hours. To the resultant solution is added 600 parts of cold water. The precipitate which forms is filtered off, washed with water, dried in air, and recrystallized from ethyl acetate to give 4',5'-dihydro-4'-hydroxyspiro[estr-4-ene-17,2'(3'H)-furan]-3-one melting at 149°–154°.

F. To a solution of 33 parts of 4',5'-dihydro-4'-hydroxyspiro[estr-4-ene-17,2'(3'H)-furan]-3-one in 790 parts of acetone is slowly added, with stirring, 42 parts of Jones' reagent. Approximately 10 minutes later, 15 parts of 2-propanol followed by 10,000 parts of water is introduced, stirring being continuous throughout. The gummy precipitate which forms is taken up in dichloromethane. The dichloromethane solution is washed with water, dried over anhydrous sodium sulfate, and stripped of solvent by vacuum distillation. The residue solidifies on contacting with hexane. Insoluble solids are filtered out and recrystallized from 3% ethyl acetate in hexane to give 4',5'-dihydrospiroestr-4-ene-17,2'(3'H).furan]-3,4'-dione.

What is claimed is:

1. A compound of the formula

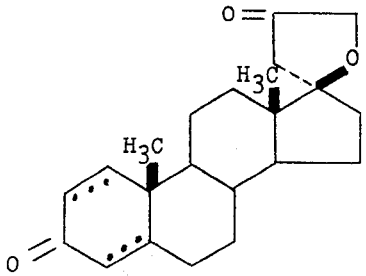

wherein the dotted lines in ring A indicate that the compound is $\Delta^1$, $\Delta^4$, or $\Delta^{1,4}$.

2. A compound according to claim 1 which is 4',5'-dihydrospiro[5α-androst-1-ene-17,2'(3'H)-furan]-3,4'-dione.

3. A compound according to claim 1 which is 4',5'-dihydrospiro[androsta-1,4-diene-17,2'(3'H)-furan]-3,4'-dione.

4. 4',5'-Dihydrospiro[5α-androstane-17,2'(3'H)-furan]-3,4'-dione.

5. 4',5'-Dihydrospiro[5α-androstane-17,2'(3'H)-furan]-3β,4'-diol.

6. 4',5'-Dihydrospiro[estr-4-ene-17,2'(3'H)-furan]-3,4'-dione.

7. A compound of the formula

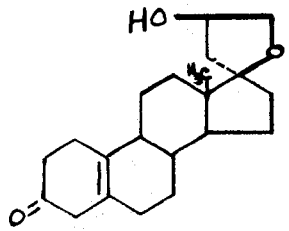

8. 4',5'-Dihydro-3-methoxyspiro[estra-2,5(10)-diene-17,2'(3'H)-furan]-4'-ol.

9. 4',5'-Dihydro-3-methoxyspiro[estra-1,3,5(10)-triene-17,2'(3'H)-furan]-4'-ol.

10. 3-Methoxyspiro[estra-1,3,5(10)-triene-17,2'(5'H)-furan].

* * * * *

UNITED STATES PATENT OFFICE
CERTIFICATE OF CORRECTION

PATENT NO. : 3939155
DATED : Feb. 17, 1976
INVENTOR(S) : Edward A. Brown

It is certified that error appears in the above-identified patent and that said Letters Patent are hereby corrected as shown below:

Abstract, Lines 2 and 3, "antiandro genic" should read -- antiandrogenic --.

Column 3, lines 3 and 4, "5α,1-7α" should read -- 5α,17α --.

Column 3, line 40, "furan[" should read -- furan] --.

Column 3, line 52, "theier" should read -- their --.

Column 4, line 35, "(3'H)" should read -- (3'H) --.

Column 4, the formula should read (in part) --

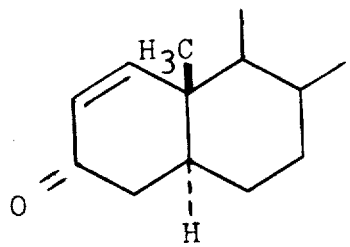

Column 6, line 30, "piroestr" should read -- piro[estr --.

Signed and Sealed this

Tenth Day of August 1976

[SEAL]

Attest:

RUTH C. MASON
Attesting Officer

C. MARSHALL DANN
Commissioner of Patents and Trademarks

UNITED STATES PATENT AND TRADEMARK OFFICE
CERTIFICATE OF CORRECTION

PATENT NO. : 3,939,155
DATED : February 17, 1976
INVENTOR(S) : Edward A. Brown

It is certified that error appears in the above-identified patent and that said Letters Patent are hereby corrected as shown below:

Column 3, line 62, "Hydroxymethyl" should read
-- hydroxymethyl --.

Column 5, line 20, "parts of 3-methoxy" should read
-- parts of 21-(hydroxymethyl)-3-methoxy --.

Signed and Sealed this

Fourteenth Day of December 1976

[SEAL]

Attest:

RUTH C. MASON
Attesting Officer

C. MARSHALL DANN
Commissioner of Patents and Trademarks